US006743435B2

(12) United States Patent
DeVore et al.

(10) Patent No.: US 6,743,435 B2
(45) Date of Patent: Jun. 1, 2004

(54) PROCESSING ANIMAL TISSUES BY DECELLULARIZING, INCREASING SURFACE AREA AND ACYLATING

(75) Inventors: Dale P. DeVore, Chelmsford, MA (US); Peter D. Ciarametaro, Gloucester, MA (US)

(73) Assignee: Collagen Matrix Technologies, Inc., Boca Raton, FL (US)

( * ) Notice: Subject to any disclaimer, the term of this patent is extended or adjusted under 35 U.S.C. 154(b) by 0 days.

(21) Appl. No.: 09/941,438

(22) Filed: Aug. 28, 2001

(65) Prior Publication Data

US 2002/0114845 A1 Aug. 22, 2002

Related U.S. Application Data

(60) Provisional application No. 60/228,393, filed on Aug. 28, 2000.

(51) Int. Cl.$^7$ .............................. A61F 2/00; A61K 38/17; C07K 1/00; C08H 1/00
(52) U.S. Cl. ...................... 424/423; 435/1.1; 530/353; 530/356; 530/402
(58) Field of Search ................. 424/93.7, 423; 435/325, 1.1; 530/356, 402, 353

(56) References Cited

U.S. PATENT DOCUMENTS

| 5,332,802 A | * | 7/1994 | Kelman et al. | ............. 530/356 |
| 5,336,616 A | * | 8/1994 | Livesey et al. | ............. 435/395 |
| 5,899,936 A | * | 5/1999 | Goldstein | ...................... 623/2 |
| 5,993,844 A | * | 11/1999 | Abraham et al. | ........... 424/423 |

* cited by examiner

*Primary Examiner*—David M. Naff
(74) *Attorney, Agent, or Firm*—Barlow, Josephs & Holmes, Ltd.

(57) ABSTRACT

Methods are provided for processing and dispersing animal tissues that involve exposing processed (e.g., decellularized) tissue to an acylating agent, wherein the ratio of acylating agent to wet tissue weight is about 0.003:1 or less. Preferably, decellularized tissue is exposed to an amount of the acylating agent of about 0.1% to about 0.3% of wet tissue weight for a time ranging from about 30 seconds to about 10 minutes. A dispersed tissue matrix is produced that has a high degree of resistance to digestion by non-collagenase proteases, such as trypsin. In order to produce sufficiently high yields of these trypsin-resistant compositions, the processed tissue is preferably cryomilled to increase its surface area prior to acylation. The dispersed acylated decellularized tissue may be in the form of an injectable composition that can be introduced into tissue of a subject.

32 Claims, No Drawings

PROCESSING ANIMAL TISSUES BY DECELLULARIZING, INCREASING SURFACE AREA AND ACYLATING

CROSS-REFERENCE TO RELATED APPLICATION

This application claims priority from U.S. Ser. No. 60/228,393, filed on Aug. 28, 2000.

FIELD OF THE INVENTION

The present invention relates to methods for processing animal tissue, particularly methods for dispersing decellularized human skin to produce injectable tissue matrix compositions.

BACKGROUND

Collagen is one of the most abundant proteins in the animal kingdom and is the primary structural component of connective tissues, such as skin, ligaments, tendons, and bones. Collagen possesses many properties, including high tensile strength, low immunogenicity, semipermeability, and solubility, that make it particularly suitable for use in the preparation of various biomaterials and other medical products, including medical prostheses, implantable compositions, cellular and acellular grafts, and other tissue replacement materials. Recently, injectable collagen formulations have been widely used in a variety of applications, including as tissue bulking compositions and as ophthalmic implants.

Collagen compositions are often prepared from skin, ligaments, or tendons by dispersion, digestion and/or dissolution. Dispersion typically involves mechanically shearing the tissue to produce a crude homogenate tissue matrix. Tissue digestion and dissolution generally entails enzyme degradation of a portion of the non-helical telopeptide portions of the collagen molecules, followed by purification steps, to produce a solution of telopeptide-poor collagen. The solubilized collagen can be reconstituted into molecular aggregates and occasional fibrils by neutralizing the enzyme digested, purified collagen solution.

Although it is generally desirable to use autologous tissues, i.e., those derived from the recipient of the implant, in the preparation of injectable collagen-containing compositions, there is seldom an ample supply of transplantable autologous tissues. Thus, allograft tissues and xenograft tissues are often used. Unfortunately, allogeneic and xenogenic tissues may be rejected by the recipient organism and may be associated with a greater risk of disease transmission. However, approximately 450,000 allograft tissues are transplanted each year in the U.S., and during the past decade, improvements in donor screening and serological testing have greatly reduced the risk of infectious disease transmission. For example, there have been no confirmed transmissions of AIDS through tissue transplants distributed by the Musculoskeletal Transplant Foundation, Edison, N.J., (MTF) in more than 10 years following the development of sensitive and accurate test methods. The estimated odds of contracting the AIDS virus from a transplant are less than 1 in 1.67 million (annual), without the inclusion of viral inactivation and sterilization steps. However, allograft implants may still be rejected following implantation. Allograft skin, used to treat burns, eventually becomes rejected, primarily due to allorecognition of Class II MHC antigens associated with Langerhans cells present in the epidermal layer of skin.

Thus, there is a need for improved methods for preparing injectable collagen compositions, particularly methods that are able to make use of allogeneic and xenogenic tissue sources while avoiding the complications that often accompany implantation of such materials.

SUMMARY OF THE INVENTION

The present invention features a method for processing dermal tissue for implantation into a subject. The method includes the steps of: (a) removing the epidermal layer of the dermal tissue to produce de-epidermalized tissue; (b) incubating the de-epidermalized tissue in at least one processing solution to remove cells from the de-epidermalized tissue, thereby producing a decellularized tissue matrix; and (c) exposing the decellularized tissue matrix to an acylating agent, wherein the ratio of acylating agent to wet tissue weight is about 0.003:1 or less. In a particularly preferred embodiment, the decellularized tissue matrix is treated, e.g., by cryomilling, to increase its surface area prior to acylation. This processing using low levels of acylating agent combined with cryomilling consistently results in relatively high yields of dispersed tissue matrix having a high resistance to trypsin.

In one embodiment of the invention, the dermal tissue is de-epidermalized by exposing the dermal tissue to a hypertonic salt solution, which allows for separation of the dermis and epidermis. The de-epidermalized tissue may then be processed by incubation in a variety of processing solutions. For example, the de-epidermalized tissue is preferably incubated in a series of decellularization solutions, including a high pH (e.g., sodium hydroxide) solution, a low pH (e.g., hydrochloric acid or phosphoric acid) solution, and a solvent (e.g., reagent alcohol). Incubation in such solutions may be in any order. For example, the de-epidermalized tissue may be incubated in low pH solutions first and then in high pH solutions and solvent solutions (or vice versa). In addition to removing cells from the tissue, this process also leads to inactivation of viruses and other contaminants in the tissue. Optionally, the tissue may be exposed to any of a number of viral inactivating agents before, during, or after the decellularization process.

In another related aspect, the invention provides a method for dispersing decellularized animal tissue, which method involves contacting any type of decellularized animal connective tissue with a solution comprising an acylating agent, wherein the ratio of acylating agent to wet tissue weight is about 0.003:1 or less. As discussed above, the decellularized tissue may be treated, for example by cryomilling, to increase the surface area of the tissue prior to decellularization.

The tissues processed according to the methods of the invention may come from autogenic, allogeneic, or xenogenic sources. In various preferred embodiments, the tissue is mammalian, preferably human; the acylating agent is an anhydride such as glutaric anhydride or succinic anhydride; and the ratio of acylating agent to wet tissue weight is within the range of about 0.002:1 to about 0.001:1.

The methods of the invention can be used to produce injectable, dispersed collagen compositions that have a trypin resistance greater than about 40%, preferably greater than about 50%, more preferably greater than about 70%, and most preferably than 90%. Preferably, the dispersed collagen matrix compositions of the invention are injectable through needles as small as 30 gauge.

In another aspect, the invention features a method of using the compositions of the invention for altering the condition of in situ tissue of a mammalian subject. The method involves placing an effective amount of the composition, e.g., as an injectable flowable mass, or formed into a putty like spreadable mass or finely divided distributable particles, at the in situ tissue site to be altered.

Other advantages and features of the present invention will be apparent from the following detailed description thereof and from the claims.

DEFINITIONS

By "acylating agent" is meant an agent that transfers an acyl group to another nucleophile. Examples of acylating agents include anhydrides, acid chlorides, sulfonyl chlorides, and sulfonic acids.

The terms "autologous" and "autogenic" refer to tissues or cells which originate with or are derived from the recipient, whereas the terms "allogeneic" and "allograft" refer to tissues or cells which originate with or are derived from a donor of the same species as the recipient. The terms "xenogenic" and "xenograft" refer to tissues or cells that originate with or are derived from a species other than that of the recipient.

By "cryomilling" is meant a reduction in size by homogenizing or pulverizing the tissue in the presence of liquid nitrogen or other such solutions that cause the tissue to remain in a frozen state during the homogenizing or pulverizing process.

By "decellularized tissue" is meant tissue that is substantially free of cells or cellular debris (i.e. a substantially acellular tissue matrix) as determined by light microscopy or by biochemical methods capable of identifying cells or cellular debris. By "substantially acellular" is meant having at least 95% fewer native cells and cell structures than the natural state of the tissue as determined by light microscopy or by biochemical methods capable of identifying cells or cellular debris.

By "processing solution" is meant a solution that is capable of inactivating viral or bacterial contaminants contained within animal tissue and/or is capable of removing cells within animal tissue while preserving the extracellular tissue matrix.

By "de-epidermalized tissue" is meant a portion of skin from which the epidermis has been substantially removed.

By "implant" is meant any biomaterial that is introduced into the body of a patient to replace or supplement the structure or function of the endogenous tissue.

By "dermal" is meant of or relating to or located in the skin. By "dermis" is meant layers of the skin underlying the epidermis and overlying the subcutaneous structures.

By "subject" is meant a mammalian organism, preferably a human or other primate species.

By "tissue" is meant an aggregation of similarly specialized cells in an organism, preferably, mammalian, and, most preferably, human, where the cells are exposed to the organism's extracellular fluid, and are united in performance of a function within an organism.

By "trypsin resistance" is meant the ability of the dispersed tissue matrix to resist digestion bytrypsin. When trypsin resistance is stated in terms of a percentage, this refers to the amount of tissue which remains undigested when exposed to 2% trypsin at 37° C. for 6–24 hours.

DETAILED DESCRIPTION

The present invention provides methods for processing animal tissues, particularly methods for preparing decellularized tissue in a form that is injectable through a cannula or through needles as small as 30 gauge. The process of the invention inactivates viral loads in tissues and effectively decellularizes tissue. Furthermore, the process produces a decellularized, injectable tissue matrix composition with high yields and with high resistance to digestion by non-collagenase proteases, such as trypsin.

The invention features methods for processing connective (collagenous) tissues, such as intact skin, from autogenic, allogenic, or xenogenic sources into a dispersed form. In the case of allogenic and xenogenic skin, methods are provided to remove epidermis, to inactivate viruses, to decellularize tissue, and to disperse the tissue via an acylation reaction into a composition retaining the characteristics and functionality of the major tissue matrix components, i.e., collagen types and collagen fibrils, elastic fiber network, and most proteoglycans, glycoproteins, and glycosaminoglycans. In addition, the dispersed matrix compositions exhibit high resistance to digestion by non-collagenase proteases and can be produced at high yields. These important properties result in part from a novel method step in which the comminuted dermis is further reduced in size by a cryomilling process prior to acylation. This cryomilling step increases the total surface area of tissue available for the acylation reaction, thereby allowing for a reduction in the amount of acylating agent needed for dispersion while maintaining high yields.

Tissue Source

The methods of the invention may be used in processing any type of connective (collagenous) tissue from autogenic, allogeneic, or xenogenic sources. While autologous tissues (transplanted from one location to another in the individual's own body) are generally regarded as the safest of all implant materials, they are not always available. Thus, allograft tissue (transplanted from one individual to another) is a preferred alternative choice for implant materials. Xenogenic sources may also be used.

The tissues used in the present invention may be derived, for example, from human, bovine, porcine, canine, ovine, caprine, equine, or other mammalian organisms. Tissue structures such as dermis, artery, vein, pericardium, heart valve, dura mater, ligament, intestine, and fascia may all be subjected to the processing techniques described herein to yield an acellular tissue matrix composition.

Human tissue for processing according to the methods of the present invention may be obtained from tissue banks or directly from hospitals. Animal tissues are obtainable from a number of meat processing companies and from suppliers of laboratory animals. Ideally, tissue procurement procedures are selected to minimize disruption of the extracellular tissue matrix or other mechanical or biochemical damaging events. The harvested tissue may be processed while still fresh or may be stored in a freezer for later processing.

Epidermis Delamination

While the present invention can be used in processing any type of connective tissue from any animal source, the preferred tissue for processing is human skin. To reduce or eliminate allorecognition of skin, it is important to remove the epidermis housing Langerhans cells. The epidermis is easily removed using a number of well-known techniques (see Skerrow & Skerrow, Chapter 23 "A survey of Methods for the Isolation and Fractionation of Epidermal Tissue and Cells" In: Methods of Skin Research, Eds: D. Skerrow and C. J. Skerrow, John Wiley & Sons, Ltd., 1985, Pp. 609–650).

For example, incubation of the skin in a hypertonic saline solution (2M NaCl) will allow for the clean separation of the epidermis and dermis without damaging the extracellular tissue matrix. The de-epidermalized skin can then be cut or macerated into appropriately sized sections or pieces for further processing.

Tissue Processing and Dispersion

In the present invention, the connective tissue (e.g., dermis) is preferably incubated in one or more processing solutions in order to inactivate viruses and other contaminants (such as bacterial or other microbial contaminants) and to remove cells (including epithelial cells, endothelial cells, smooth muscle cells, and fibroblasts) from the tissue while maintaining the structural integrity of the extracellular (e.g., collagenous) tissue components, thereby producing a decellularized tissue matrix. A variety of well-known chemical, biochemical, and physical methods may be used to accomplish decellularization. These techniques include, but are not limited to, incubation in certain salts, detergents, or enzymes, radiation exposure, vapor freezing, hypotonic lysis, and treatment with acidic and/or alkaline solutions (see, e.g., U.S. Pat. Nos. 5,192,312, 5,336,616, 5,993,844, 5,613,982). Whatever decellularization technique is employed, it preferably should not disrupt or substantially alter the biomechanical properties of the structural elements of the tissue. In a preferred embodiment, the tissue is treated with a high pH solution, followed by treatment in a low pH solution and then by treatment is a solvent solution, thereby inactivating viral contaminants and removing cells from the tissue. This approach has the advantage of producing a substantially acellular tissue matrix that is free of detergents, enzymatic modifications, or other unwanted effects that can be associated with other methods of decellularization.

Methods for preparing and utilizing tissue compositions that include implantable, cross-linkable, telopeptide-containing, naturally crosslinked human collagen derived from comminuted intact human tissue are well-known in the art. (See, e.g., U.S. Pat. Nos. 4,969,912 and 5,332,802, both of which are incorporated herein by reference.) Such compositions are prepared by reacting comminuted tissues with an amine acylating agent or a carboxylic reactive esterifying agent or combination thereof at weight ratios of amine reactive acylating agent to wet tissue of from about 0.005:1 to about 0.5:1. Such preparations can be utilized for altering the condition of autogenic or allogenic in situ tissue.

In the present invention, dispersion of decellularized tissue is accomplished via an acylation step. Without being bound to a particular theory, we posit that such dispersion occurs as the acylating agent reacts with nonspecific, deprotonated proteins binding matrix collagen fibrils together in fibers and fiber bundles. Some acylation of collagen fibrils also occurs. Excess acylation of collagen matrix structures causes destabilization of such reacted collagen fibrils resulting in sensitivity to digestion by noncollagenase proteases, such as trypsin. Trypsin generally is ineffective at digesting intact collagen structures. The acylation reaction is also rapid, probably complete within 1 minute. Since acylating reagents are water sensitive, they rapidly undergo hydrolysis into acid forms. Thus, there is competition between reacting with deprotonated amines and undergoing hydrolysis. The acylation reaction must be carefully controlled to allow enough reactivity to disperse the tissue matrix but not to allow too much reactivity such that the collagen fibril matrix is destabilized and subject to digestion by noncollagenase proteases.

We have found that the dispersion reaction can be optimized to allow effective tissue dispersion while maintaining the integrity and structure of the collagenous matrix. In the present invention, this is accomplished by increasing the surface area of the tissue prior to acylation and by decreasing the ratio of amine acylating agent to wet tissue to levels of about 0.004:1 or less, preferably less than 0.003:1, and most preferably from about 0.002:1 to about 0.001:1. As shown in the Examples below, dispersed dermis prepared using such improvements exhibit significantly higher yields, higher resistance to trypsin, and greater clinical longevity than dispersed dermis prepared using previously described methods (for example, U.S. Pat. No. 5,332,802). Typically, dispersed dermis prepared by the methods of the invention exhibit a trypsin resistance greater than about 40%, preferably greater than about 50%, most preferably greater than about 70% or 90%.

In order to increase the surface area of the tissue prior to acylation, the processed (decellularized) tissue is preferably subjected to a cryomilling process, which involves, for example, placing coarsely macerated treated dermis in a stainless steel container containing a level of liquid nitrogen approximately 1 inch over the tissue; holding the tissue in a frozen state for at least 10 minutes; macerating the frozen tissue for several bursts of 1–3 minutes each in a maceration chamber using a static rotor/stator macerator/size reduction apparatus while maintaining the macerated tissue in a frozen state by adding more liquid nitrogen. An example of such an apparatus is the TEKMAR® Analytical Mill for milling dry or frozen tissues. Alternatively, other techniques for increasing the surface area of the processed tissue may be employed, such as mincing the tissue, microfluidization (forcing coarse macerated tissue through sequentially smaller diameter cannula to decrease particle size), sonication, and other such methods to reduce particle size. Increasing the surface area of the tissue prior to acylation increases the effectiveness of the dispersion process, thus allowing lower amounts of acylating agent to be used while still achieving relatively high product yields. This reduction in the amount of acylating agent, in turn, leads to greater trypsin resistance in the dispersed tissue.

A preferred acylating reaction for the dispersion of processed (decellularized) tissue is acylation with glutaric anhydride or succinic anhydride. However, any acylating agent may be used for the dispersion reaction, for example, any anhydride, acid chloride, sulfonyl chloride, or sulfonic acid may be used. All of these acylating agents work by reacting with, and derivatizing, the deprotonated free amines of a protein. In many cases, the free amine group is derivatized with a chemical moiety that provides an anionic group, thereby reducing the pKa of the protein. For certain proteins, such as collagen, this also renders the protein more soluble at physiological pH.

In general, the acylating agent may be an aliphatic or aromatic, mono-, di-, or higher functional carboxylic acid anhydride, ester or halide; or sulfonic acid or halide, such as a lower alkanoic, lower alkane-dioic, or higher functional lower alkane carboxylic, or aryl mono-, di-, or higher functional carboxylic (e.g., benzoic or naphthoic), acid anhydride, ester or halide, or lower alkyl, or aryl (e.g., phenyl or naphthyl), mono-, di-, or higher functional sulfonic acid or halide, to provide the corresponding acyl (carbonyl or sulfonyl) moiety on the amine group, for example, lower alkanoyl, aroyl (e.g., phenoyl or naphthoyl), alkyl sulfonyl, aryl (e.g., phenyl or naphthyl), sulfonyl, or substituted amino (amido or sulfonamido).

The acylating agent may be added directly to a reaction mixture as a solid material (e.g., a powder) or dissolved in a suitable organic solvent such as acetone, N,N- dimethylformamide (DMF), ethanol, or methyl pyrrolidone. The total quantity of acylating agent depends on the extent of modification required or desired. As discussed above, the quantity of acylating agent required should generally satisfy the weight ratio of acylating agent to wet tissue of approximately 0.004:1 or less (i.e., less than or equal to 0.4% of wet tissue weight), preferably less than 0.003:1 (i.e., less than 0.3%), and most preferably from about 0.002:1 to about 0.001:1 (i.e., between 0.2% and 0.1%).

Using any of the above reagents, the acylation reaction (i.e., the amine modifying reaction) generally proceeds within a pH range of 7 to 11, although it is preferably carried out at a mildly basic pH (for example, pH 8–10, and, more preferably 8.5–9) to increase the reaction speed and reduce the processing time. For acylating the free amine groups on proteins associated with tissues, an acylation buffer at physiological pH is preferably utilized.

The reaction time for acylation of collagen will vary according to a number of factors including, for example, the amount of collagen to be acylated, the type of acylating agent, the pH, and the temperature of the reaction mixture. In addition, the method of addition of the acylating agent to the collagen composition will affect the reaction time. For example, addition of the acylating agent as a solid or in an appropriate solution will increase and decrease the reaction time, respectively. The reaction time is generally slower if the acylating agents are added as solids or powders.

In general, the acylation reaction should proceed to completion within a time ranging from about 30 seconds to about 10 minutes following each addition, preferably from about 1 to about 5 minutes. The reaction will generally occur at any reaction temperature between about 0° C. to about 45° C., but is preferably effected at about 20° C. to about 37° C., and especially at room temperature (about 25° C.) for greatest convenience.

In addition to the above-mentioned methods, the acylation methods provided in any of DeVore et al. and Kelman et al., U.S. Pat. Nos. 5,492,135; 5,104,957; 5,201,764; 4,969,912, 5,332,802 and 5,480,427, may also be utilized, and these patents are incorporated herein by reference.

In one embodiment of the invention, following treatment with the acylation agent, the fine macerated, dispersed dermis is preferably subjected to additional static homogenization, subjected to filtration though a fine mesh screen, recovered by centrifugation, mixed to ensure homogeneity, and filled into syringes for clinical administration. Once the dispersed tissue matrix is prepared, it may be subjected to additional treatments to introduce intramolecular and/or intermolecular crosslinks to further stabilize the dispersion, rending it even more resistant to enzymatic digestion. Such treatments may include glutaraldehyde, EDAC {1-ethyl-3-(-3-dimethylaminopropyl)carbodiimide}, and other standard chemicals and reagents commonly used to crosslink collagen.

The injectable, dispersed collagen matrix compositions produced by the methods of the invention have a variety of clinical uses, particularly as therapeutic or cosmetic implants. For example, the compositions of the invention may be used as intradermal implants to augment soft connective tissue or to correct skin defects such as wrinkles and scars. The compositions are also useful as injections into vocal folds to treat dysphonia or glottic insufficiency, as injections into submucosa of the urethra to treat urinary incontinence due to intrinsic sphincter deficiency, and as injectable drug delivery systems for localized drug administration. Other uses include replacement, augmentation, or other alteration of the condition of connective tissue, for example, in the form of a material for skin grafts, matrix substances or components for cell seeding and grafting, a material matrix for tissue "putty" or filler, and the like.

The features and other details of the invention will now be more particularly described and pointed out in the following examples describing preferred techniques and experimental results. These examples are provided for the purpose of illustrating the invention and should not be construed as limiting.

EXAMPLE 1

PROCESSING HUMAN DERMAL TISSUE

Human cadaveric skin was procured from tissue banks or organ and tissue procurement organizations complying with standards established by the American Association of Tissue Banks and regulations mandated by the FDA in 21 C.F.R. § 21, Part 1270. Human skin was either provided fresh or frozen. If provided fresh, the skin was washed in physiological medium, subjected to controlled freeze-down and stored at −80° C.

Skin Processing: Frozen skin was removed from the −80° C. freezer and allowed to thaw at refrigeration or room temperatures. The skin was then placed in a hypertonic saline solution (2M NaCl) to facilitate epidermal removal. The de-epidermalized skin was then macerated into pieces approximately 1-4 mm square and soaked in three consecutive solutions for viral inactivation. The first solution was 0.5M NaOH, the second 0.5M phosphoric acid, and the third reagent alcohol. For optimal dispersion, the virally inactivated, decellularized, macerated dermis was subjected to cryomilling using a standard tissue mill. Liquid nitrogen was placed in the mill with the macerated dermis. The resulting milled dermis was generally less than 1 mm square. If not milled, the macerated only dermis was approximately 1–4 mm square. Either "macerated only" or "macerated and milled" dermis was then treated with an acylating agent (usually glutaric anhydride) prepared in reagent alcohol. The acylating agent was added to either "macerated only" or "macerated and milled" dermis. The standard concentration of glutaric anhydride with "macerated and milled" dermis was 0.2% of wet tissue weight or about 0.002:1. This same concentration was also used with "macerated only" dermis. Dispersed matrix yields were significantly reduced with "macerated only" dermis. If higher concentrations of the acylating were used with "macerated only" dermis, yields were higher but sensitivity to trypsin was also higher indicating destabilization of the collagen fibril network. The reacted dermis was then subjected to additional mechanical maceration or pulverization to allow effective tissue dispersion. The resulting dispersed dermis was collected by centrifugation, washed with 0.004M phosphate buffer, recovered by centrifugation, sized by filtration through 100–250$\mu$ pore-size filters (229±25 $\mu$m, 152±25 $\mu$m pore size filters in series), mixed, extruded through a 30 gauge cannula, and placed in syringes.

Results show that the addition of cryomilling and a reduction in the concentration of acylating agent greatly improve dispersed matrix yield and resistance to digestion by trypsin. Cryomilling alone produced significant improvements in product yield and resistance to trypsin. Reductions in the ratio of acylating agent to wet tissue had little effect on milled tissue yield. However, trypsin resistance was increased as shown in Table 1.

TABLE 1

Effects of Cryomilling on Product Yield and Trypsin Resistance

| Process | Source | N | GA (%) | Bulk Yield (m/g dermis) | | Final Product Trypsin (%) | |
|---|---|---|---|---|---|---|---|
| | | | | AVE | Range | AVE | Range |
| CryoMilled | Proc. Dev. | 4 | 0.16 | 59 | 48–73 | 69.8 | 63–76 |
| CryoMilled | Proc. Dev. | 6 | 0.20 | 43 | 30–70 | 58 | 51–63 |
| CryoMilled | Production | 54/52/26 | 0.20 | 45 | 26–72 | 54 | 26–75 |
| Nonmilled | Production | 146/169/169 | 0.20 | 16 | 4–46 | 41 | 18–65 |

As shown in Table 1, milling increased both product yield and trypsin resistance. Reducing the concentration of acylating agent (glutaric anhydride) from 0.20% to 0.16% resulted in an increase in trypsin resistance.

EXAMPLE 2

EVALUATION OF CLINICAL RELEVANCE OF HIGHER TRYPSIN RESISTANCE

Dispersed allogeneic human dermis with low and high trypsin resistance was implanted in rabbit ears. About 0.35 cc of either low or high trypsin resistance human dermis was injected into rabbit ears. The volume of each injectate was measured using caliphers at weekly intervals up to 8 weeks. At each interval, the measured size of the injectate was larger for the high trypsin injectate than for the low trypsin injectate.

EXAMPLE 3

CLINICAL RELEVANCE OF HIGHER TRYPSIN RESISTANCE

Clinical evaluation of dispersed allogeneic human dermis was conducted in a controlled clinical study. Both low and high trypsin resistant dispersed human dermis were evaluated. Clinical results shown below demonstrate that the higher trypsin resistant dispersed human dermis provided better clinical correction when injected into dermal defects than lower trypsin resistant dispersed human dermis.

TABLE 2

Effect of Trypsin Resistance on Clinical Effectiveness.

| Trypsin Resistance (%) | # Pts. | Average Correction @ 1 Month | Average Correction @ 3- Months | Average Correction @ 6- Months | Average Correction @ 9- Months |
|---|---|---|---|---|---|
| 44% | 3 | 80% | 77% | 37% | 15% |
| 85% | 5 | 100% | 86% | 74% | 45% |

Table 2 demonstrates the importance of trypsin resistance to clinical effectiveness. This degree of trypsin resistance can be achieved by controlling the quantity of acylating agent during tissue dispersion. Table 1 demonstrates the effectiveness of the cryomilling step in producing an acceptable yield of high trypsin resistant dispersed dermis. Thus, these date demonstrate that both cryomilling and controlled acylation are important steps in preparing commercial quantities of injectable dispersed human dermis having high trypsin resistance.

EXAMPLE 4

EFFECT OF CRYOMILLING ON THE COMPOSITION OF DISPERSED DERMIS

Dispersed dermis prepared with and without cryomilling was biochemically evaluated by SDS PAGE, and by SDS PAGE following treatment with cyanogens bromide. Additional evaluations include measurement of fat content, GAG content, and DNA content. All evaluations demonstrated that cryomilled and nonmilled dispersed dermis exhibited nearly identical matrix composition (Table 3).

TABLE 3

Composition of Dispersed Allogeneic Human Dermis Prepared with and without Cryomilling.

| Component | Macerated Only | Macerated & CryoMilled |
|---|---|---|
| Total Collagen | 40–50 mg/mL | 45–55 mg/mL |
| Type I Collagen | 60–70% | 60–70% |
| Type III Collagen | 10–20% | 10–20% |
| Other Collagens | ~10% | ~10% |
| Elastin | <0.5% | <0.5% |
| GAGs | 1.81 ± 0.52 mg/mL | 1.42 ± 0.11 mg/mL |
| Fat | <0.1% | <0.1% |
| DNA | <750 ng/mL | <750 ng/mL |

Thus, the combination of cryomilling and reduced quantities of acylating agents produced a superior dispersed human dermal preparation that would not be obtainable using methods in the prior art. For example, U.S. Pat. No. 5,332,802, does not describe the use of cryomilling to reduce particle size before reaction with acylating agents and does not describe the use of limited quantities of acylating agents to cause dispersion of comminuted tissue. In fact, it teaches that the quantity of acylating agent should be from 0.005:1 to 0.5:1. Quantities as high as 0.005:1 will not reliably produce a dispersed product that is as resistant to noncollagenase proteases as the present invention. As demonstrated by the Examples herein, reducing the quantity of acylating agent to 0.002:1 results in a product that is more clinically effective. In order for a reduction to this level of acylating agent to be practicable (i.e. produce commercially viable yields), the tissue is cryomilled to increase exposed area before the acylating reaction, thus providing suitable yields of dispersed tissue.

EXAMPLE 5

DISPERSION OF HUMAN CARTILAGE

Human cartilage was extracted during surgical rhinoplasty procedures. Specimens were frozen in sterile saline prior to processing. Specimens were incubated in reagent alcohol for 24 hours after being washed twice in reagent alcohol. Alcohol was removed and the specimens rinsed two times in 0.004M phosphate buffer at pH 7.0–7.8 and then incubated in the same buffer for 16–18 hours. The 0.004M phosphate buffer was removed and the tissues soaked in 0.02M disodium phosphate at pH 9.0. Tissue was not subjected to cryomilling but was minced using scissors into small pieces. Acylating agent was added to the tissue during pulverization or homogenization. Effects of different ratios of acylating agent to wet tissue were evaluated. Dispersed cartilage was evaluated by SDS PAGE and by transmission electron microscopy. Samples of dispersed cartilage were also examined for resistance to digestion by trypsin. Results are shown below.

TABLE 4

Effects of acylating agent percent on characteristics of dispersed human cartilage.

| Sample | % acylating agent | Yield (mg/mL) | Trypsin Resistance |
|---|---|---|---|
| Set 1 | 0.165 (0.00165:1) | 27.6 | 84+ |
| Set 2 | 0.205 (0.00205:1) | 37.8 | 92.5 |
| Set 3 | 0.240 (0.0024:1) | 49.2 | 66.6 |

Table 4 shows that the quantity of acylating agent affects both the yield and the trypsin resistance of the dispersed cartilage. At a ratio of 0.00205:1, the yield was only 37.8 mg/mL. However, trypsin resistance was 92.5%. (Note that only one of three samples treated at 0.165% was available for trypsin testing. Yields of the other two samples were too low for further testing). As the ratio was increased to 0.00240:1 the yield increased to 49.2 mg/mL as the trypsin resistance decreased to 66.6%. The dispersed cartilage exhibited intact collagen fibrils and showed predominantly Type II collagen by SDS PAGE. It is expected that cryomilling prior to acylating dispersion would increase yields at the lower ratio of acylating agent to wet tissue.

EXAMPLE 6

DISPERSION OF IN VITRO FORMED TISSUE MATRIX

In vitro produced tissue matrix was provided in sheet form. The matrix was physically removed from the synthetic sheet backing and mixed in 0.02M phosphate buffer at pH 9.0. The macerated tissue matrix was then dispersed by reaction with acylating agent at 0.01% to 0.03% (% wet weight of matrix). The mixture was subjected to homogenization during the acylating reaction to facilitate dispersion. The dispersed tissue matrix was recovered by centrifugation, washed with 0.004M phosphate buffer, filtered through a 100μ pore size filter, collected by centrifugation, mixed, passed through a 30 gauge cannula and placed in syringes. Dispersed in vitro produced tissue matrix was evaluated biochemically and examined by light microscopy and transmission electron microscopy. TEM showed the presence of intact collagen fibrils. Biochemical analysis demonstrated the predominant presence of Type I collagen. Analysis of trypsin resistance showed that controlled acylation (0.01% or 0.0001:1, ratio of acylating agent to wet tissue weight) provided a trypsin resistance level of about 70%. If excess acylation was conducted (0.03% or 0.0003:1, ratio of acylating agent to wet tissue weight), trypsin resistance was reduced to only 30%. Again controlled acylation provided an injectable tissue matrix prepared from in vitro produced tissue matrix.

As the above examples illustrate, in order to obtain trypsin-resistant material at sufficient yields to be commercially practicable, a combination of cryomilling the tissue followed by acylation with a low concentration of acylating agent is preferably employed. The results obtained from the combination of these techniques were generally superior to those obtained from either technique alone.

OTHER EMBODIMENTS

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein. Such equivalents are intended to be encompassed in the scope of the present invention.

All references, including patents, publications and patent applications, mentioned in this specification are herein incorporated by reference to the same extent as if each independent publication, patent or patent application was specifically and individually indicated to be incorporated by reference.

We claim:

1. A method for processing dermal tissue for implantation into a subject, said method comprising the steps of:
   a. removing the epidermal layer of said dermal tissue to produce de-epidermalized tissue;
   b. incubating said de-epidermalized tissue in at least one processing solution to remove cells from said de-epidermalized tissue, thereby producing a decellularized tissue matrix;
   c. treating said decellularized tissue matrix to cause a reduction in size and an increase in surface area; and
   d. exposing said treated decellularized tissue matrix to an acylating agent for a time ranging from about 30 seconds to about 10 minutes, wherein the amount of said acylating agent is about 0.1% to about 0.3% of wet tissue weight, thereby producing a dispersed tissue matrix.

2. The method of claim 1, wherein said treating comprises cryomilling said decellularized tissue matrix.

3. The method of claim 1, further comprising contacting said de-epidermalized tissue with a viral inactivating agent, before, after, or during step (b).

4. The method of claim 1, wherein said tissue is mammalian.

5. The method of claim 3, wherein said tissue is human.

6. The method of claim 1, wherein said acylating agent is glutaric anhydride or succinic anhydride.

7. The method of claim 1, wherein said amount of acylating agent is about 0.1% to about 0.2% of wet tissue weight.

8. The method of claim 1, wherein said processing solution comprises sodium hydroxide.

9. The method of claim 1, wherein said processing solution comprises phosphoric acid.

10. The method of claim 1, wherein said tissue is autogenic, allogeneic or xenogeneic.

11. The method of claim 1, wherein said step of removing the epidermal layer comprises exposing said tissue to a hypertonic salt solution.

12. A method for dispersing decellularized animal connective tissue, said method comprising the steps of:
   treating said decellularized animal connective tissue to cause a reduction in size and an increase in surface area; and
   contacting said treated decellularized, animal connective tissue with a solution comprising an acylating agent for a time ranging from about 30 seconds to about 10 minutes, wherein the amount of said acylating agent is about 0.1% to about 0.3% of wet tissue weight.

13. The method of claim 12, wherein said treating comprises cryomilling said decellularized tissue.

14. The method of claim 12, wherein said tissue is mammalian.

15. The method of claim 12, wherein said tissue is human.

16. The method of claim 12, wherein said tissue is dermal tissue.

17. The method of claim 12, wherein said amount of acylating agent is about 0.1% to about 0.2% of wet tissue weight.

18. A method for augmenting the condition of in situ tissue of a subject, said method comprising introducing an effective amount of a dispersed collagen matrix into said in situ tissue of said subject, said dispersed collagen matrix being prepared by treating a decellularized animal connective tissue matrix to cause a reduction in size and an increase in surface area and contacting said treated decellularized, animal connective tissue matrix with a solution comprising an acylating agent for a time ranging from about 30 seconds to about 10 minutes, wherein the amount of said acylating agent is about 0.1% to about 0.3% of wet tissue weight.

19. The method of claim 18, wherein said subject is a human.

20. The method of claim 18, wherein said dispersed collagen matrix is derived from an allogeneic source.

21. The method of claim 18, wherein said acylating agent is glutaric anhydride or succinic anhydride.

22. The method of claim 18, wherein said amount of acylating agent is about 0.1% to about 0.2% of wet tissue weight.

23. A composition comprising an injectable, dispersed collagen matrix prepared by treating a decellularized animal connective tissue matrix to cause a reduction in size and an increase in surface area and contacting said treated decellularized animal connective tissue with a solution comprising an acylating agent for a time ranging from about 30 seconds to about 10 minutes, wherein the amount of said acylating agent is about 0.1% to about 0.3% of wet tissue weight.

24. The composition of claim 23, wherein the dispersed collagen matrix is injectable through a 30 gauge needle.

25. The composition of claim 23, wherein the dispersed collagen matrix has a trypsin resistance such that greater than about 40% of the dispersed collagen matrix remains undigested when exposed to 2% trypsin at 37° C. for 6–24 hours.

26. The composition of claim 23, wherein the dispersed collagen matrix has a trypsin resistance such that greater than about 50% of the dispersed collagen matrix remains undigested when exposed to 2% trypsin at 37° C. for 6–24 hours.

27. The composition of claim 24, wherein the dispersed collagen matrix has a trypsin resistance such that greater than about 70% of the dispersed collagen matrix remains undigested when exposed to 2% trypsin at 37° C. for 6–24 hours.

28. The composition of claim 24, wherein the dispersed collagen matrix has a trypsin resistance such that greater that about 90% of the dispersed collagen matrix remains undigested when exposed to 2% trypsin at 37° C. for 6–24 hours.

29. An injectable composition comprising decellularized, acylated, dispersed, dermal tissue matrix comprising a collagen matrix, said tissue being acylated with an acylating agent in an amount of about 0.1% to about 0.3% of wet tissue weight for a time ranging from about 30 seconds to about 10 minutes and having a trypsin resistance such that greater than about 40% of the collagen matrix remains undigested when exposed to 2% trypsin at 37° C. for 6–24 hours.

30. The composition of claim 29, wherein the dermal tissue matrix has a trypsin resistance such that greater than about 50% of the collagen matrix remains undigested when exposed to 2% trypsin at 37° C. for 6–24 hours.

31. The composition of claim 29, wherein the dermal tissue matrix has a trypsin resistance such that greater than about 70% of the collagen matrix remains undigested when exposed to 2% trypsin at 37° C. for 6–24 hours.

32. The composition of claim 29, wherein the dermal tissue matrix has a trypsin resistance such that greater than about 90% of the collagen matrix remains undigested when exposed to 2% trypsin at 37° C. for 6–24 hours.

* * * * *